United States Patent [19]
Klaiber et al.

[11] Patent Number: 5,938,669
[45] Date of Patent: Aug. 17, 1999

[54] ADJUSTABLE GASTRIC BANDING DEVICE FOR CONTRACTING A PATIENT'S STOMACH

[75] Inventors: Christian Klaiber, Aarberg; Sker de Salis, Neuchâtel; Stephan Siegenthaler, Utzenstorf, all of Switzerland

[73] Assignee: Klasamed S.A., Neuchatel, Switzerland

[21] Appl. No.: 09/055,700

[22] Filed: Apr. 7, 1998

[30] Foreign Application Priority Data

May 7, 1997 [EP] European Pat. Off. ............. 97810287

[51] Int. Cl.[6] .................................................. A61B 17/00
[52] U.S. Cl. ............................ 606/157; 600/31; 604/909
[58] Field of Search .................................. 606/201, 202, 606/203, 151, 157; 604/909; 600/29, 30, 31, 37, 593; 128/95.1, 96.1, 118.1, 847, 887

[56] References Cited

U.S. PATENT DOCUMENTS

| | | |
|---|---|---|
| 3,750,194 | 8/1973 | Summers ........................................ 3/1 |
| 3,863,622 | 2/1975 | Buuck . | |
| 5,152,770 | 10/1992 | Bengmark et al. ..................... 606/157 |
| 5,449,368 | 9/1995 | Kuzmak . | |
| 5,771,903 | 6/1998 | Jakobsson ............................... 128/898 |

FOREIGN PATENT DOCUMENTS

| | | |
|---|---|---|
| 1174814 | 12/1969 | European Pat. Off. . |
| 202815 | 11/1986 | European Pat. Off. . |

*Primary Examiner*—Michael Buiz
*Assistant Examiner*—Jennifer Maynard
*Attorney, Agent, or Firm*—Sughrue, Mion, Zinn, Macpeak & Seas, PLLC

[57] ABSTRACT

An adjustable gastric banding device is used for contracting a patient's stomach in order to fight obesity. A gastric band (1) of a known type, implanted around the stomach and including a cavity (2) filled with liquid, is connected by a tube (7) to a control box (9) and a balancing reservoir (11) which are implanted under the patient's skin. The box (9) contains an electric pump and an electronic control unit capable of communicating by radio with a monitor (13) carried by the patient and with a controller (12) intended for the doctor. The controller can operate the pump by remote control to transfer determined volumes of liquid in a closed circuit from the gastric band to the reservoir or vice versa, to adjust the diameter of a passage in the stomach. The monitor receives and signals alarms from the control box.

12 Claims, 3 Drawing Sheets

ADJUSTABLE GASTRIC BANDING DEVICE FOR CONTRACTING A PATIENT'S STOMACH

FIELD OF THE INVENTION

The present invention concerns an adjustable gastric banding device for contracting a patient's stomach, including a gastric band intended to be implanted around the patient's stomach and having a cavity of variable volume filled with a liquid, and means for adjusting the volume of the liquid in said cavity, including a control box intended to be implanted in the patient's body and connected to the gastric band cavity by a tube.

DESCRIPTION OF THE PRIOR ART

Such a device can be used in a known method for fighting obesity, called "Adjustable Gastric Banding", consisting of constricting an upper part of the patient's stomach for several months or years by means of a gastric band implanted to form a passage (stoma) in the stomach of small diameter which limits the speed of ingestion of food. This diameter can be adjusted as a function of the patient's progress, by removing or adding liquid to the variable volume cavity of the gastric band.

Gastric bands of this type are disclosed in U.S. Pat. Nos. 4,592,339, 4,696,288, 5,074,868 and 5,449,368, and in International Patent Application Nos. WO 86/04498 and WO 94/27504. They can be used within the scope of the present invention.

The device disclosed in U.S. Pat. No. 4,592,339 usually includes, in the guise of a control box for adjusting the volume of liquid, an injection unit directly implanted under the patient's skin and provided with a self-sealing membrane. The inside of this unit is connected to the gastric band by a flexible tube. By pricking a syringe needle through the skin and the membrane, the doctor can inject additional liquid or, conversely, remove some, in order to change the opening of the passage into the stomach as required.

The main drawback of these devices of the prior art is that, in order to adjust the volume of liquid in the gastric band, the withdrawing or addition of liquid has to be carried out externally by means of a syringe, which each time involves the injection of a needle, discomfort and the risk of infection for the patient. Moreover, the risk of liquid escaping through the self-sealing membrane is not negligible. Another risk is that a non-authorised person could, simply using a syringe, change the volume of liquid without the knowledge of the doctor concerned and thus disturb the treatment.

SUMMARY OF THE INVENTION

An object of the present invention is to overcome this drawback, by providing a gastric banding device which can be adjusted in a non-invasive manner and without causing discomfort for the patient. A particular object consists of providing a device which offers increased safety when used, in particular by allowing its operation to be monitored in a non-invasive manner, alarm signals to be given and non-authorised interventions to be prevented.

Generally, the invention concerns an adjustable banding device of the type indicated in the preamble, wherein said device also includes a reservoir, intended to be implanted in the patient's body and connected to the control box or incorporated therein, and in that the control box includes an electric power source, an electronic control unit and an electrically powered pump which is controlled by the control unit for transferring liquid in a closed circuit between the reservoir and the cavity of the gastric band.

Thus the device according to the invention can operate during its entire period of service with a constant volume of liquid, adjustments being effected by transfers of predetermined volumes of liquid in a closed circuit between the gastric band and the reservoir by means of a control box which is implanted in the body like a pace-maker and which, when necessary, may be remote controlled in a non-invasive manner through the patient's skin. The expression "closed circuit" illustrates that an unvarying volume of liquid is contained in a closed unit of chambers and tubes forming a hydrostatic circuit without communication of fluid with the exterior of said unit, which is entirely implanted in the patient's body.

Use of a pump connected to a compensation reservoir and implanted in the human body has already been proposed for opening and closing an artificial sphincter. For example, U.S. Pat. No. 3,750,194 discloses a non-motorised pump having a magnetised rotor which is magnetically driven in rotation from outside the body to reversibly close a natural or implanted body passage, in particular a urinary passage or the alimentary canal. However, such a device cannot be used with gastric banding, because it operates on an "all or nothing" basis, i.e. it closes or opens the body passage, but cannot adjust a degree to which said passage is open. Conversely, the gastric banding method requires the passage into the stomach always to be open, to a precise and constant degree, and the adjustment of such opening to be made via transfer of a known quantity of liquid.

Use of a motorised pump, preferably a positive displacement pump, associated with an electric power source and an electronic control unit in an assembly implanted in the body constitutes a secure method for controlling the volumes transferred by the pump, and thus also the size of the passage into the stomach. This size and the variations which the doctor imposes thereon are essential parameters in treatment by gastric banding. Moreover, one must be sure that the gastric passage is never closed.

The adjustment means preferably include a control apparatus, also called a controller, situated outside the patient's body, and the control unit and the controller include cordless communication means, in particular, radio-frequency means, for transmitting data to each other. A doctor can thus operate the pump by remote control using the controller to transfer liquid between the gastric band and the reservoir. Moreover, he can transmit data and commands to the control unit and receive data therefrom to check its proper operation.

In particular, the control unit is preferably arranged so as to transmit via said cordless communication means an indication of the transferred volume of liquid. The controller thus receives feedback from the system implanted in the body, allowing the operation thereof to be monitored, the volumes transferred to be accurately recorded, and thus the state of the system to be known at any time, in particular the volume of liquid present in the gastric band.

In the preferred embodiment, the control box includes a pressure sensor indicating the pressure of the liquid in the tube to the control unit, and the control unit is arranged for producing an alarm signal when said pressure departs from a predetermined range. The limit values of this range are stored in a memory of the control unit and can be changed by radio by means of the controller.

The device according to the invention may further include a monitor situated outside the patient's body and provided with cordless means for communicating with the control unit, the monitor having display means which are activated in response to picking up said alarm signal.

In a particular embodiment, the pump is capable of operating selectively in opposite directions, to pump liquid either in the direction of the gastric band, or in the direction of the reservoir.

The present invention further concerns a method for treating obesity by adjustable gastric banding, including the steps of :

(i) implanting in a patient's body an assembly including : a gastric band arranged around the patient's stomach and provided with a cavity of variable volume filled with a liquid, a reservoir, a control box and a liquid circuit connecting the gastric band cavity to the reservoir via the control box, said box including an electric power source, an electronic control unit and an electric pump arranged in the liquid circuit;

(ii) adjusting the gastric band cavity volume by transferring a volume of liquid between said cavity and the reservoir by means of the pump, the transfer being controlled in a non-invasive manner by cordless communication between a control apparatus placed outside the patient's body and said electronic control unit.

BRIEF DESCRIPTION OF THE DRAWINGS

Other features and advantages of the present invention will appear in the following description of a preferred embodiment, given by way of non-limiting example with reference to the appended drawings, in which.

DESCRIPTION OF THE PREFERRED EMBODIMENTS

Figure 1:
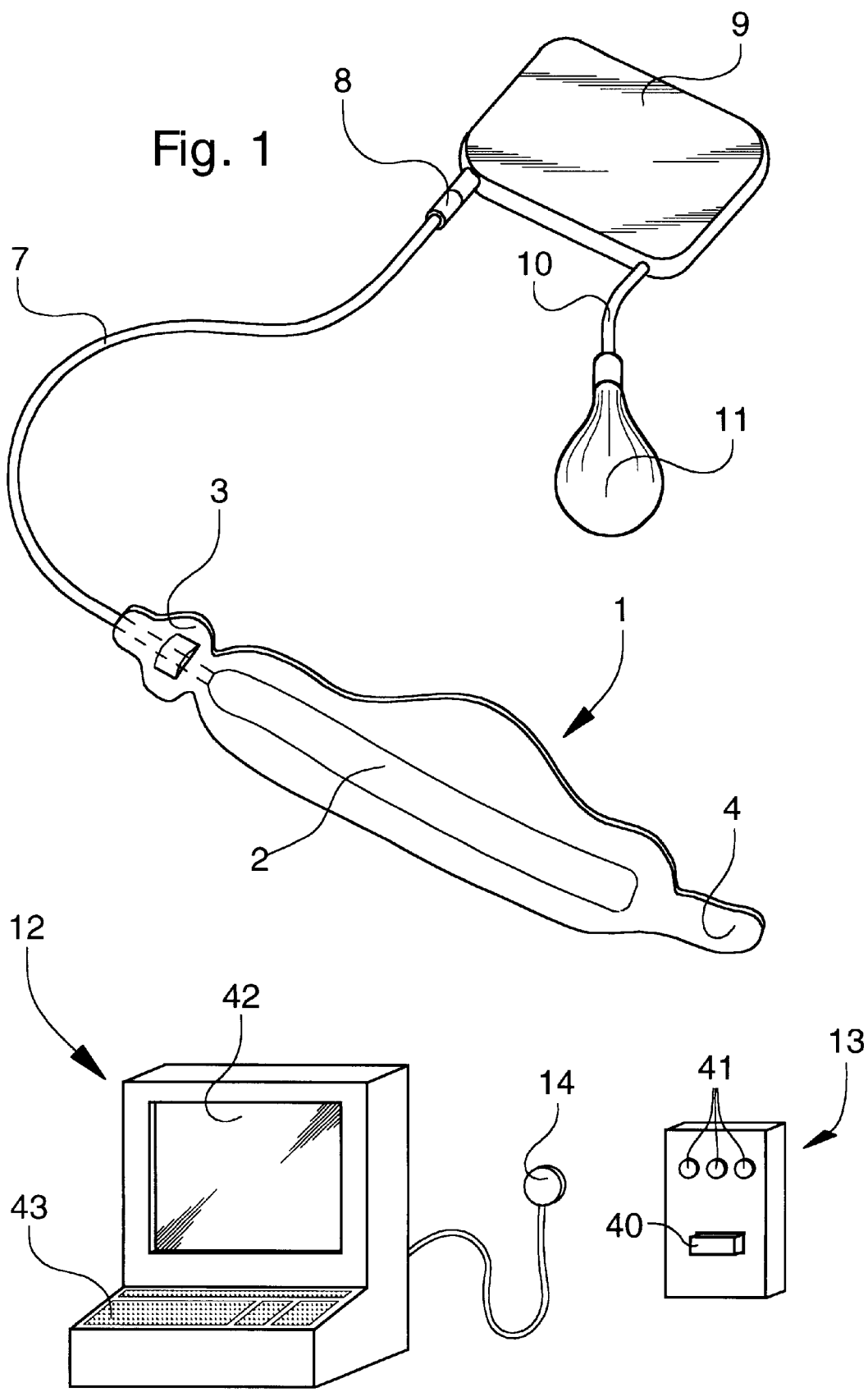
FIG. 1 is a schematic overall view of the device according to the invention.
Figure 2:
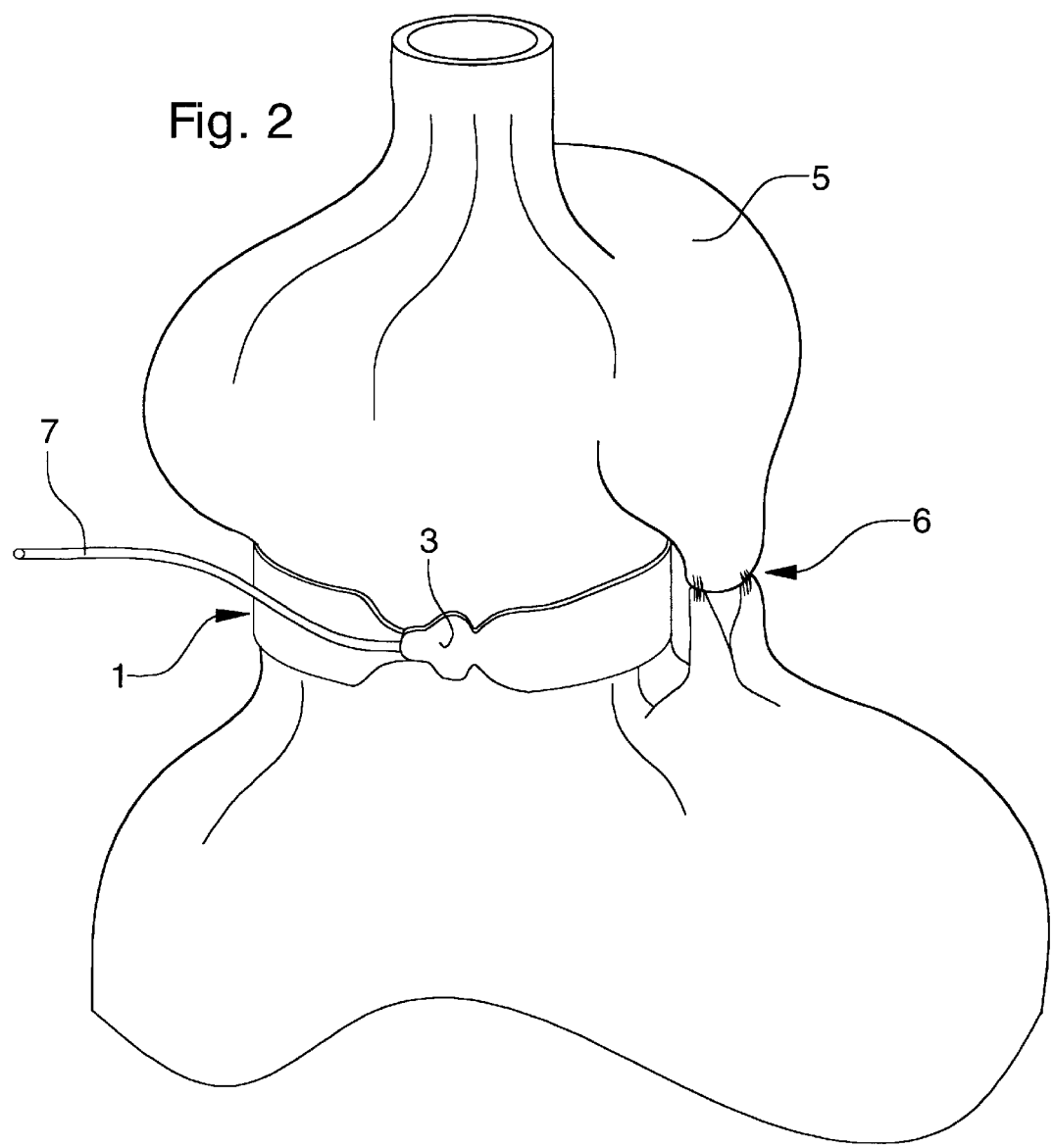
FIG. 2 is a perspective view of the gastric band fixed onto the stomach.

FIG. 1 shows all the main components of the device according to the invention. A gastric band 1, which may be for example one of the types described in the aforementioned prior art Patents, includes a flexible wall on its inner face, which delimits a cavity 2 filled with a variable volume of liquid. The ends 3 and 4 of band 1 are provided with fastening elements of a known type, allowing such ends to be fixed to each other once band 1 has been placed around an upper part 5 of the patient's stomach, as is shown by FIG. 2. A stitch 6 is preferably made on the external wall of the stomach to hold the band in place.

FIG. 1 shows that end 3 of band 1 is connected to a flexible tube 7 the other end of which is connected by a self-sealing connector 8 to a control box 9. This box is also connected via a tube 10 to a balancing reservoir 11 which also contains a variable volume of liquid and which communicates with cavity 2 of band 1 via tube 10, box 9 and tube 7. Box 9 contains means allowing liquid to be transferred from reservoir 11 to cavity 2 and vice versa.

Reservoir 11 is preferably made in the shape of a soft pouch placed in proximity to control box 9. It could also be placed directly on a face of said box or within said box.

Control box 9 and reservoir 11 are implanted in the patient's body in a suitable place, which may be away from the stomach, for example directly under the patient's skin so that box 9 is easily accessible as required. Given that this box contains electromagnetic means for communicating with the exterior, as will be described hereinafter, subcutaneous implantation is preferable and also allows the box and the reservoir to be easily replaced if necessary.

The other components of the device shown in FIG. 1 are a controller 12 and a monitor 13 which are situated outside the patient's body. Each of these two apparatus is arranged to communicate with control box 9 by electromagnetic means, for example by radio. Controller 12 is intended for the doctor concerned. It may have the appearance of a micro-computer fitted with a radio transceiver having an antenna 14 which can be fixed on the patient's body in front of box 9. Monitor 13, which has approximately the size of a matchbox, is intended for the patient, who will carry it on him or keep it close at hand. Monitor 13 can communicate with box 9 via a transmission system similar to that of controller 12. It will be noted however that monitor 13 is not an essential element in the embodiment described here.

Figure 3:
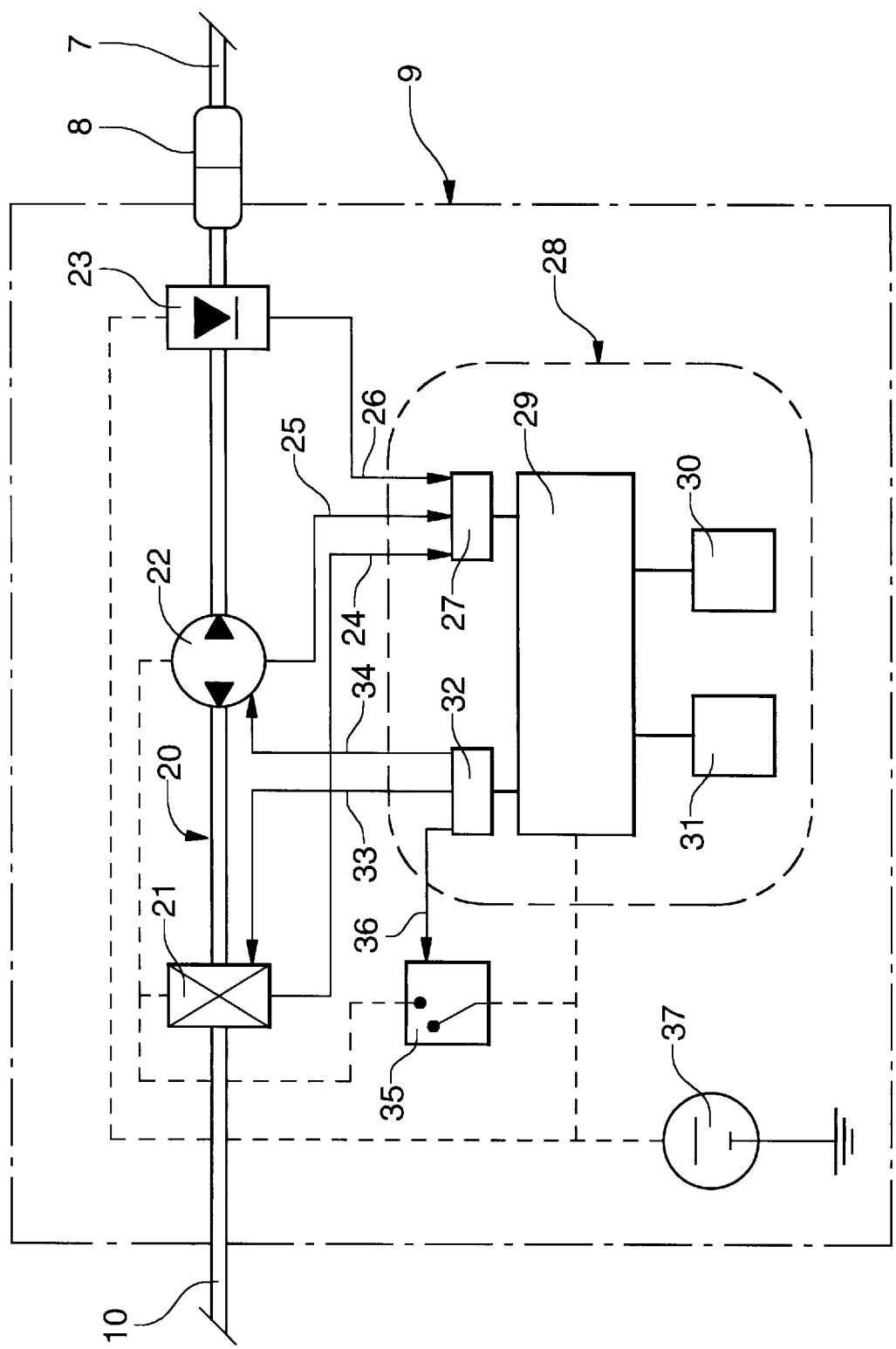
FIG. 3 is a block diagram of the control box.

FIG. 3 shows schematically the main operational elements contained in control box 9. Tube 10 which comes from reservoir 11 is connected to connector 8 of tube 7 by a liquid circuit 20 on which are mounted in series an electrovalve 21, an electric motor pump 22 and a pressure sensor 23. These three elements are connected by electric lines 24, 25 and 26 to inputs 27 of an electronic control unit 28 including a logic circuit 29, formed for example by an integrated circuit such as a microprocessor and coupled to an external memory 30 and a radio transceiver 31 provided with an antenna which is not shown. Control unit 28 further includes outputs 32 connected to electrovalve 21 and pump 22 by electric control lines 33 and 34, and to relays 35 by an electric control line 36.

Pump 22 is preferably a positive displacement pump capable of pumping in both directions, for example a peristaltic pump. The operating direction may change simply by inverting the motor supply polarity.

Control box 9 further includes an electric battery 37 which supplies, by lines shown in dotted lines, control unit 28 and pressure sensor 23, and electrovalve 21 and pump 22 via relay 35 controlled by unit 28. This relay is usually open in order to save energy; it is only closed when electrovalve 21 and/or pump 22 have to be actuated.

Control unit 28 receives a signal via line 24 indicating whether electrovalve 21 is open or closed, a signal via line 25 indicating whether pump 22 is working or not, and in which direction, and a signal via line 26 indicating the pressure of the liquid in tube 7 and thus in cavity 2 of gastric band 1. Unit 28 controls the opening and closing of electrovalve 21 via line 33, the starting, direction of pumping and stopping of pump 21 via line 34, and the opening and closing of relay 35 via line 36.

The normal state of control box 9 is a stand-by state. Electrovalve 21 is closed and pump 22 is switched off, so that the respective volumes of liquid in cavity 2 of the gastric band and in reservoir 11 are invariable. Since relay 35 is open, only unit 28 and pressure sensor 23 are supplied by battery 37. Transceiver 31 is ready to pick up signals. Unit 28 permanently monitors the essential parameters, which are:

the pressure of the liquid in the circuit, such pressure having to remain between a minimum value and a maximum value which are predetermined and stored in a programmable part of memory 30;

the voltage of battery 38;

the presence of any short-circuit;

the result of a self-diagnosing programme.

Moreover, unit 28 emits at periodic intervals, for example twice a day, via transceiver 31, an interrogation signal intended to check whether monitor 13 is within reach of radio transmission and in operating state, in order to encourage the patient to keep the monitor with him. If, for example, two interrogations are fruitless, monitor 13 is programmed to emit an alarm signal which can be repeated until the patient or his entourage reacts: by bringing the monitor back close to the patient, a signal can be sent from the monitor to control box 9 to reestablish the connection, which will stop the alarm.

In FIG. 1, it will be noted that the monitor is fitted with a control button 40, to generate transmission of a radio signal to box 9, and with three light-emitting diodes 41 acting as operating and alarm indicators.

If the monitoring performed by control unit 28 detects an anomaly in the aforementioned essential parameters, unit 28 will generate the following actions:

1. Activation of the transmission mode of transceiver 31.
2. Transmission of a brief signal to activate an alarm code in monitor 13 corresponding to the defective parameter.
3. The different possible alarms are displayed on monitor 13 by means of combinations of diodes 41.
4. Monitor 13 acknowledges pick-up of the alarm to control unit 28. The combination of diodes will remain illuminated until monitor is reset to its initial state by controller 12.
5. Transceiver 31 is reset to pick-up mode.

This sequence is arranged to reduce as much as possible the periods of transmission of transceiver 31, in order to save the energy of battery 37, while assuring optimum operating safety of the device.

Monitor 13 also preferably contains a micro-processor and has a self diagnosing system available, which is independent of box 9, in particular for monitoring the state of its battery, which the patient can easily change himself.

When the patient visits his doctor, either because his monitor 13 has signalled an alarm, or for a routine check-up, the doctor uses controller 12 to intervene in the part of the device implanted in the patient's body. Several types of intervention are possible.

First of all, controller 12 will identify the patient. For this purpose, each control unit 28 contains, in the non-programmable and thus non changeable part of memory 30, a personal identification number (PIN) known to the doctor and patient. This code may further be marked on the case of monitor 13. The identification sequence is as follows:

1. The doctor enters the PIN in controller 12 and starts the identification process.
2. Controller 12 communicates the PIN to unit 28.
3. Unit 28 compares the PIN received to that which it contains in its memory.
4. Unit 28 communicates the result of the comparison to controller 12.

If the result is positive, the doctor can begin intervention. The following operations A to E may be carried out:

A. Confirmation of alarm

Controller 12 asks unit 28 to repeat the last alarm which it gave. On this basis, the doctor decides the intervention which follows. For example, if battery 37 is dead, he will change the control box.

B. Modification of the limit pressure values

Controller 12 communicates the new limit values to unit 28, and unit 28 stores them in memory 30 and acknowledges receipt.

C. Transfer of liquid

Controller 12 communicates the quantity and direction of transfer to unit 28. Unit 28 then starts the following sequence:

1. Applying voltage to electrovalve 21 and pump 22 by relay 35.
2. Opening of electrovalve 21.
3. Starting of pump 22 in the desired direction and for the necessary duration, corresponding to the volume to be transferred. At the same time, the doctor can check the size of the passage into the stomach by means of a gastrostenometer inserted via the oesophagus.
4. Stopping of pump 22.
5. Closing of electrovalve 21.
6. Disconnection of the electrovalve and the pump.
7. Communication of completed transfer acknowledgement to the controller. Moreover, this communication may include an indication of the volume of liquid transferred.

D. Setting to stand-by mode

Controller 12 transmits an end of intervention signal. Unit 28 then carries out the following diagnostic sequence checking points 2 to 6 hereinafter.

1. Setting of the transceiver in transmission mode.
2. Relay 37 open.
3. Electrovalve 21 closed.
4. Pump 22 switched off.
5. Pressure measured by sensor 23 within the stored limits.
6. State of battery 37.
7. Transmission of a successful or unsuccessful diagnosis signal.
8. Setting of transceiver 31 into pick-up mode.

The doctor can thus take a decision as a function of the result of the diagnosis.

E. Preparation for changing the control box

Changing control box 9 requires local surgical intervention with an incision into the patient's skin. In order to avoid any problems when connector 8 is disconnected and box 9 and reservoir 11 are manipulated, controller 12 blocks all the functions of control box 9, except the pick-up function of transceiver 31 (to allow unblocking if the blocking is due to an error).

The structure of monitor 13 shown in FIG. 1 is not described here in detail, since a man skilled in the art can produce it without difficulty on the basis of the functions described in this application. Of course, it contains a radio transceiver for communicating with control box 9. The operation of monitor 13 is carried out under the control of the same personal identification code (PIN) as control box 9, in order to avoid mixing up patients.

Controller 12 preferably includes a screen 42 for displaying data, a keyboard 43 for data input and function control, and sufficient memories for storing personal data for each patient, his personal identification code, the limit pressure values stored in control box 9, the transfers of liquid effected, the dates and nature of interventions. It may also communicate by radio with monitor 13 to reset the latter to its initial state after picking up one or more alarms. Controller 12 may also include an interface for connection to a computer, for example in order to store data therein, or be directly incorporated in a computer.

The present invention is not limited to the embodiment described hereinbefore, but it may be subject to multiple modifications or alternatives. For example, two-directional pump 22 shown in FIG. 3 may be replaced by the arrangement shown in FIG. 4, including a one-directional electric pump 44. Tube 20a connected to reservoir 11 and tube 20b connected to gastric band 1 are selectively connected to pump 44 via a three-position hydraulic valve 45 or by an equivalent arrangement of valves, controlled by unit 28 via an electric line 46. In its neutral position shown in FIG. 4, valve 45 closes tubes 20a and 20b, so that it replaces electrovalve 21. Its two other positions allow the transfer of liquid via pump 44, respectively in one direction and the other.

Figure 4:
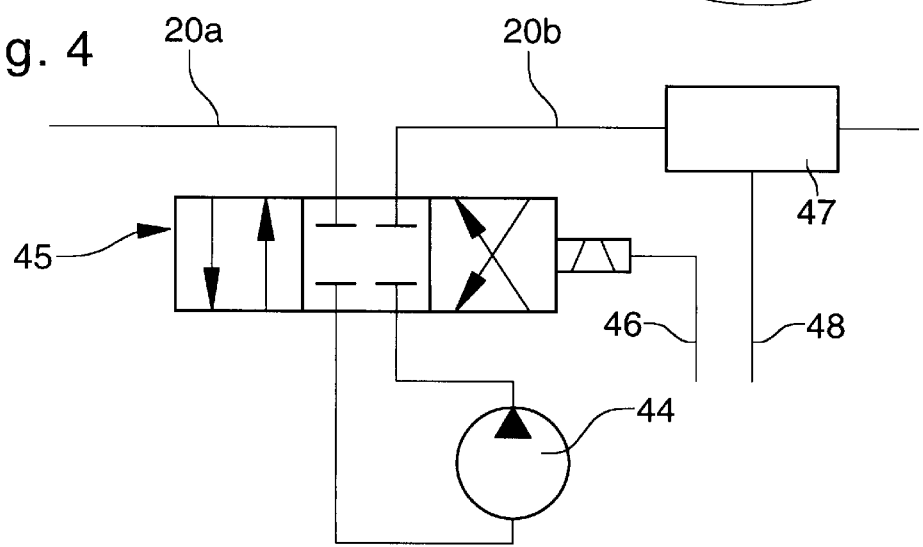
FIG. 4 is a diagram showing a modification of the embodiment shown in FIG. 3.

FIG. 4 also shows a flow meter 47 associated with tube 20b and connected via an electric line 48 to unit 28 to indicate to the latter the flow of liquid transferred by pump 44. Such a flow meter may also be installed in circuit 20 in the case of FIG. 3. It is necessary when pump 22 or 44 is not a positive displacement pump, but it may also be provided in combination with a positive displacement pump.

What is claimed is:

1. Adjustable gastric banding device for contracting a patient's stomach, including :
    a gastric band intended to be implanted around the patient's stomach and having a cavity of variable volume filled with a liquid; and
    means for adjusting the volume of liquid in said cavity, including a control box intended to be implanted in the patient's body and connected to said cavity of said gastric band by a tube;
    wherein said device further includes a reservoir, intended to be implanted in the patient's body and connected to said control box or incorporated therein, and wherein said control box includes an electric power source, an electronic control unit and an electrically driven pump controlled by said control unit for transferring liquid in a closed circuit between said reservoir and said cavity of the gastric band.

2. Device according to claim 1, wherein said pump is a positive displacement pump.

3. Device according to claim 1, wherein said control box includes means for measuring the volume of liquid transferred by said pump.

4. Device according to claim 1, wherein said means for adjusting the volume further include a control apparatus, situated outside the patient's body, and in that said control unit and said control apparatus include cordless communication means for transmitting data to each other.

5. Device according to claim 4, wherein said data includes a personal identification code stored in said control unit.

6. Device according to claim 4, wherein said control unit is arranged to transmit an indication of the volume of liquid transferred via said cordless communication means.

7. Device according to claim 4, wherein said control box includes a pressure sensor indicating the pressure of the liquid in said tube to said control unit, and wherein said control unit is arranged to generate an alarm signal when said pressure departs from a predetermined range.

8. Device according to claim 7, further including a monitor situated outside the patient's body and provided with cordless means for communicating with said control unit, said monitor having display means which are activated in response to picking up said alarm signal.

9. Device according to claim 1, wherein said pump is capable of operating selectively in opposite directions, to pump liquid either in the direction of said gastric band, or in the direction of said reservoir.

10. Device according to claim 1, wherein an electrovalve controlled by said control unit is connected in series between said reservoir and said pump.

11. Method for treating obesity by adjustable gastric banding, including the steps of:
    (i) implanting in a patient's body an assembly including : a gastric band arranged around the patient's stomach and provided with a cavity of variable volume filled with a liquid, a reservoir, a control box, and a liquid circuit connecting said gastric band cavity to said reservoir via said control box, said box including an electric power source, an electronic control unit and an electric pump arranged in said liquid circuit;
    (ii) adjusting the gastric band cavity volume by transferring a volume of liquid between said cavity and said reservoir by means of said pump, the transfer being controlled in a non-invasive manner by cordless communication between a control apparatus placed outside the patient's body and said electronic control unit.

12. Method according to claim 11, wherein a measurement of the volume of transferred liquid is effected in said control box and transmitted to said control apparatus via said cordless communication.

\* \* \* \* \*